(12) United States Patent  (10) Patent No.: US 8,801,740 B2
Koike et al.  (45) Date of Patent: Aug. 12, 2014

(54) ADJUSTABLE LANCING DEVICE

(75) Inventors: Masufumi Koike, Kyoto (JP); Masahiro Fukuzawa, Kyoto (JP)

(73) Assignee: Arkray, Inc., Kyoto (JP)

( * ) Notice: Subject to any disclaimer, the term of this patent is extended or adjusted under 35 U.S.C. 154(b) by 1253 days.

(21) Appl. No.: 10/483,205

(22) PCT Filed: Jul. 10, 2002

(86) PCT No.: PCT/JP02/07029
§ 371 (c)(1),
(2), (4) Date: Jan. 7, 2004

(87) PCT Pub. No.: WO03/005906
PCT Pub. Date: Jan. 23, 2003

(65) Prior Publication Data
US 2004/0186500 A1  Sep. 23, 2004

(30) Foreign Application Priority Data

Jul. 11, 2001  (JP) ................. 2001-211248

(51) Int. Cl.
*A61B 17/32*  (2006.01)
(52) U.S. Cl.
USPC ........................... 606/181; 606/182
(58) Field of Classification Search
USPC ................ 606/181, 182, 170–172, 166–167, 606/185–189, 576, 151; 600/573, 583, 576, 600/293; 30/293, 320; 604/187, 272
See application file for complete search history.

(56) References Cited

U.S. PATENT DOCUMENTS

| 4,730,613 | A | * | 3/1988 | Gordy ........................... 606/172 |
| 5,318,584 | A | * | 6/1994 | Lange et al. .................. 606/182 |
| 5,443,198 | A | * | 8/1995 | Viola et al. ................. 227/179.1 |
| 5,613,978 | A | * | 3/1997 | Harding ........................ 606/181 |
| 5,730,753 | A | * | 3/1998 | Morita ........................ 606/181 |
| 6,156,051 | A | * | 12/2000 | Schraga ........................ 606/181 |
| 6,419,661 | B1 | * | 7/2002 | Kuhr et al. .................... 604/207 |
| 6,558,402 | B1 | * | 5/2003 | Chelak et al. ................. 606/182 |

FOREIGN PATENT DOCUMENTS

| JP | 10-508527 | 8/1998 |
| JP | 11-9577 | 1/1999 |
| JP | 2000-11678 | 4/2000 |
| JP | 2000-254113 | 9/2000 |

* cited by examiner

*Primary Examiner* — Darwin Erezo
*Assistant Examiner* — Diane Yabut
(74) *Attorney, Agent, or Firm* — Studebaker & Brackett PC

(57) ABSTRACT

A lancing device (A) includes a lancing adjustment mechanism for adjusting the lancing depth of a lancet (L) into a target portion (99) by operating an operation member (20c). The lancing adjustment mechanism is designed to provide a nonlinear relationship between the lancing depth of the lancet (L) into the target portion (99) and the operation amount of the operation member (20c). With this arrangement, it is possible to suitably adjust bleeding at the lanced portion, thereby improving the operationality of the lancing device (A).

12 Claims, 7 Drawing Sheets

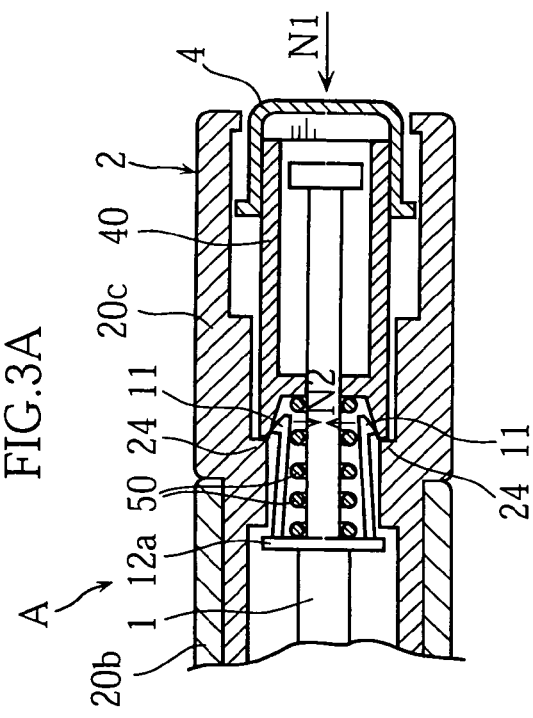
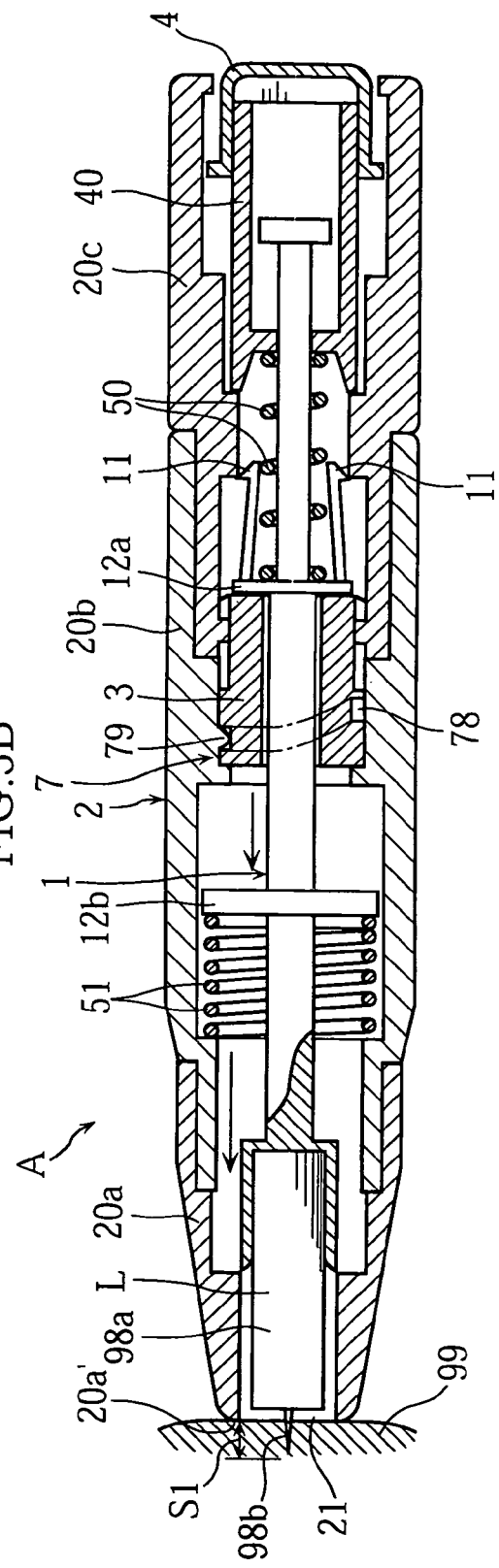

ADJUSTABLE LANCING DEVICE

TECHNICAL FIELD

The present invention relates to a lancing device used for sticking a tip end of a lancet into skin for taking blood or other body fluid or tissue for examination.

BACKGROUND ART

A conventional lancing device generally has a basic structure in which a lancet holder holds a lancet in a housing to advance the lancet holder toward a tip end portion of the housing by resilient force generated by a predetermined operation of a spring. The forward movement of the lancet holder is performed with the tip end portion of the lancet holder pressed against the skin of the human body. The tip end portion of the lancet can be stuck into the skin of the human body to cause bleeding from the skin. The blood is taken as a sample for examination.

When a lancing device is used for sticking a lancet into the skin as described above, it is desirable for the lancet to be made adjustable in terms of the lancing depth into the skin for preventing the user from experiencing great pain or for avoiding excess or deficiency of the bleeding from the skin. Some of prior art lancets can be adjustable in the lancing depth into skin by the lancet (see JP-A-H11-9577 for example).

However, the prior art device has the following problems.

In recent years, the necessary amount of sample for precise analysis has been decreasing due to rapid improvement in performance of an analyzer used for sample analysis. This seems to be the trend for the future. The decrease in the necessary amount of sample analysis results in decrease in the bleeding amount by lancing. It follows that the lancet sticks just slightly into skin.

However, in the prior art, the adjustment rate of the lancing depth of the lancet is constant both in increasing and reducing the lancing depth of the lancet. Therefore, when the lancing depth of the lancet should be made small to cause slight bleeding from the skin, the lancing depth is adjusted with the same rate as in the case where the lancing depth of the lancet is large. Generally, when the lancing depth into the skin by the lancet is made relatively large, the increase in the bleeding amount is not precisely proportional to the increase in the lancing depth. On the other hand, when the lancing depth into the skin by the lancet is small, the lancing depth is relatively precisely proportional to the bleeding amount. In light of these, when a slight amount of bleeding is needed, it is desirable that the lancing depth of the lancet is adjusted more fine than in the case where a large amount of bleeding is needed. However, the above-described prior art device does not meet such requirements.

SUMMARY OF THE INVENTION

It is therefore an object of the present invention to provide a lancing device capable of eliminating or at least lessening the above-described problems.

A lancing device according to the present invention may comprise:

a housing having an open tip end;

an operation mechanism for advancing a lancet from inside the housing toward the tip end of the housing; and a lancing adjustment mechanism including an operation member which is operated for adjusting a lancing depth of the lancet into a target portion upon forward movement of the lancet.

The above-mentioned lancing adjustment mechanism provides a nonlinear relationship between the lancing depth of the lancet and an operation amount of the operation member.

"The nonlinear relationship" means that a line plotted in rectangular coordinates having two perpendicular axes is not a single straight line, but a curved or polygonal line, for example.

Preferably, the lancing adjustment mechanism is so designed that the lancing depth varies at a lower rate for a given operation amount of the operation member when the lancing depth of the lancet into the target portion is smaller than when the lancing depth is larger.

Preferably, the lancing adjustment mechanism is capable of providing a state in which a tip end of the lancet does not project beyond the tip end of the housing upon forward movement of the lancet.

Preferably, the lancing depth adjustable mechanism selectively provides a first state in which a tip end of the forwardly moved lancet projects out beyond the tip end of the housing and a second state in which the forwardly moved lancet does not project out, the lancing depth varying at a lower rate for a given operation amount of the operation member in the second state than in the first state.

Preferably, the lancing adjustment mechanism includes a stopper for stopping the forward movement of the lancet by contacting the lancet or a member forwardly movable with the lancet.

The above-mentioned stopper may be reciprocally movable axially of the housing by operating the operation member.

Preferably, the operation member may be a rotatable sleeve.

The stopper may be arranged in the housing to rotate together with the sleeve when the sleeve is rotated.

The housing and the stopper may be formed with a cam groove and a projection for moving the stopper axially of the housing, the projection engaging in the cam groove.

Preferably, the cam groove may have different inclination angles toward a forward and a rear ends, respectively, of the housing.

Preferably, the sleeve may form a part of the housing.

Preferably, the lancing adjustment mechanism may include an auxiliary member fowardly movable together with the lancet within the housing toward the tip end of the housing. The auxiliary member may have a tip end flanking a tip end of the lancet.

The lancet may project beyond the tip end of the auxiliary member by an amount which is variable by operating the operation member.

Preferably, the tip end of the auxiliary member may be cylindrical to surround the tip end of the lancet.

Preferably, the operation mechanism may comprise a lancet holder arranged in the housing for holding and advancing the lancet.

The operation member may be a rotatable sleeve.

The auxiliary member may be fitted into the lancet holder to rotate together with the sleeve when the sleeve is rotated.

The auxiliary member and the lancet holder may be formed with a cam surface and a projection contacting each other for moving the auxiliary member axially of the housing by rotating the auxiliary member.

Preferably, the cam surface may have different angles toward a forward and a rear ends, respectively, of the housing.

Preferably, the housing may include a first sleeve forming the tip end of the housing and a second sleeve connected to a rear end of the first sleeve.

The lancing adjustment mechanism may enable the first sleeve to move reciprocally relative to the second sleeve axially of the housing by rotating the first sleeve relative to the second sleeve.

Preferably, the lancing adjustment mechanism may comprise a cam mechanism including a cam groove and a projection formed on the first sleeve and the second sleeve. The projection engages in the cam groove, and the cam groove has different angles toward a forward and a rear ends, respectively, of the housing. Other features and advantages of the present invention will become clearer from the detailed description given below with reference to the accompanying drawings.

BRIEF DESCRIPTION OF THE DRAWINGS

FIGS. 3A and 3B are explanatory views illustrating an operation of the lancing device shown in FIG. 1.

MODE FOR CARRYING OUT THE INVENTION

Figure 1:
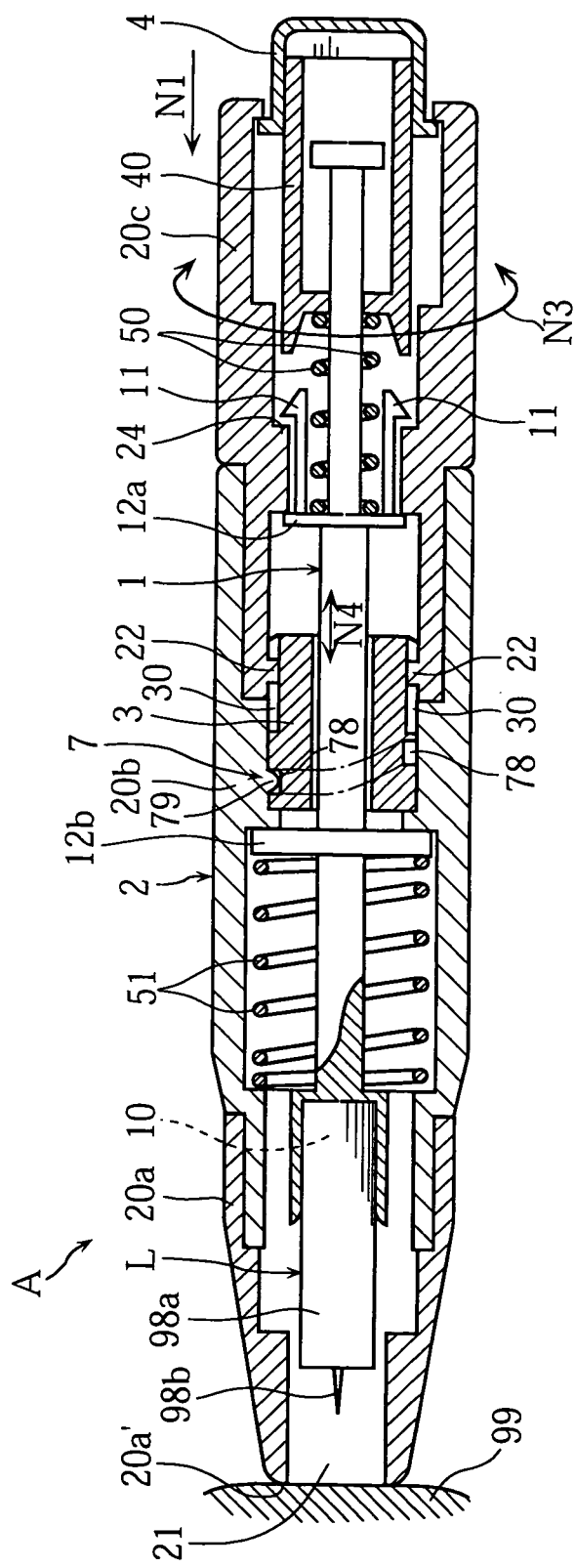
FIG. 1 is a sectional view showing a lancing device according to a first embodiment of the present invention.
Figure 2:
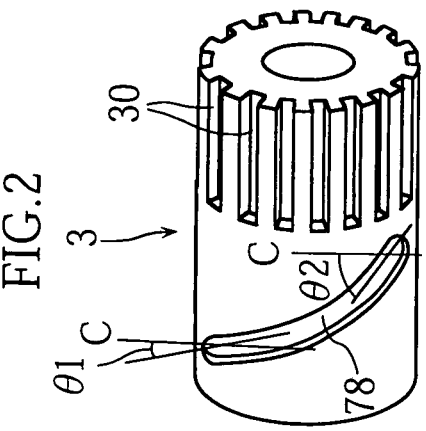
FIG. 2 is a perspective view showing a stopper used for the lancing device shown in FIG. 1.

Preferred embodiments of the present invention will be described below with reference to the accompanying drawings.

FIGS. 1 through 4 show a first embodiment of the present invention. As clearly shown in FIG. 1, a lancing device A of the present embodiment includes a lancet holder 1 for holding a lancet L, a housing 2 internally accommodating the lancet holder 1, a stopper 3, a cam mechanism 7 and a pusher cap 4.

The lancet L has a main body 98a made of synthetic resin. The main body includes a tip end surface from which a metal needle 98b projects.

The housing 2 comprises, for example, three sleeves 20a-20c connected to each other in series and has a generally cylindrical configuration having a tip end formed with an opening 21. The sleeve 20a constitutes a tip portion of the housing 2. As described later, when the lancing device A is used for lancing, the tip end 20a' of the sleeve 20a is pressed against the skin 99, which is a lancing target. Since the sampled body fluid may adhere to the sleeve 20a, it is preferable that the sleeve 20a be removable from the sleeve 20b for replacement. The sleeves 20b and 20c are connected so as to be rotatable relative to each other about their axis. As more specifically described later, the lancing depth of the lancet L into the skin 99 can be adjusted by rotating the sleeve 20c of the lancing device A.

The lancet holder 1 extends in the axial direction of the housing 2 and includes a recess 10 for holding the lancet L fitted therein, a plurality of latch pawls 11, and a first and a second flanges 12a, 12b. The latch pawls 11 are capable of engaging with a step 24 provided on an inner surface of the sleeve 20c. This engagement can latch the lancet holder 1 in a predetermined position within the housing 2.

The latched lancet holder 1 can be released by pressing forward the pusher cap 4. More specifically, the pusher cap 4 is slidable relative to the sleeve 20c. When the pusher cap 4 is pressed forward in the direction of an arrow N1, as shown in FIG. 3A, the latch pawls 11 are pressed forward by the tip end portion of a pressing member 40 fitted into the pusher cap 4. This pressing operation causes the respective latch pawls 11 to be deformed in the radius direction of the housing 2 for releasing the engagement with the step 24. As moving forward, the pusher cap 4 compresses a spring 50 arranged between the first flange 12a and the pressing member 40. As shown in FIG. 3B, when the engagement between the latch pawls 11 and the step 24 is released, the lancet holder 1 is flung toward the opening 21 of the housing 2 by the restoring force of the spring 50. A return spring 51 is provided in front of the second flange 12b. The spring 51 is compressed by the lancet holder 1 moving forward, and then, after the lancet L sticks into the skin, the spring exerts repulsive force that causes the lancet holder 1 to retreat by an appropriate amount.

The stopper 3, which is generally cylindrical, is accommodated in the housing 2 and slidably fitted around a shaft of the lancet holder 1. As clearly shown in FIG. 3B, the stopper 3 is located in front of the first flange 12a to stop the forward movement of the lancet holder 1 by contacting the first flange 12a. As clearly shown in FIG. 2, the stopper 3 has an outer circumferential surface formed with a plurality of spline grooves 30 and one or a plurality of cam grooves 78. As shown in FIG. 1, the tip end portion of the sleeve 20c has an inner circumferential surface formed with a plurality of projections 22 fitting into the respective spline grooves 30. Thus, the sleeve 20c and the stopper 3 are not rotatable relative to each other. Therefore, when the sleeve 20c is rotated relative to the sleeve 20b in the direction of an arrow N3, the stopper 3 is rotated together.

The cam mechanism 7 has a structure in which the cam groove 78 is engaged with a projection 79 formed on the inner circumferential surface of the sleeve 20b. The cam groove 78 is inclined relative to the axial direction of the stopper 3 and the lancet holder 1. Therefore, when the sleeve 20c is operated to rotate the stopper 3 relative to the sleeve 20b, the stopper 3 moves in the axial direction of the lancet holder 1 indicated by an arrow N4 due to the guiding function by the projection 79 and the cam groove 78. It should be noted that the inclination angle of the cam groove 78 is not constant but gradually becomes gentler (tends to be perpendicular to the axial direction of the stopper 3 and the lancet holder 1) as proceeding toward the front of the lancing device A. More specifically, in FIG. 2, the cam groove 78 is inclined relative to a line C perpendicular to the axial direction of the stopper 3 so that the inclination angle $\theta 2$ closer to the rear of the stopper 3 is greater than the inclination angle $\theta 1$ closer to the front of the stopper. In this structure, the lancing depth into skin by the lancet L is in nonlinear relationship with the rotating of the sleeve 20c. In the present embodiment, the cam groove 78 is formed in the stopper 3, and the projection 79 is formed on the sleeve 20b. Conversely, the projection 79 may be formed on the stopper 3, and the cam groove 78 may be formed in the sleeve 20b in the present invention. In the lancing device A according to the present invention, the rotation of the sleeve 20c causes the stopper 3 to move by the cam mechanism 7. This mechanism is an example of the lancing adjustment mechanism of the present invention.

Next, the operation of the lancing device A will be described.

In the use of the lancing device A, as shown in FIG. 1, the tip end of the housing 2 is brought into contact with the skin 99, and then the pusher cap 4 is pressed down. Consequently, as shown in FIGS. 3A and 3B, the lancet holder 1 advances by the resilient force of the spring 50, whereby the needle 98b of the lancet holder sticks into the skin 99. As described above, the lancet holder 1 moves forward before the first flange 12a contacts the stopper 3. The stopper 3 prevents further forward movement. Further, the stopper 3 can be shifted in position in the axial direction of the housing 2 by rotating the sleeve 20c relative to the sleeve 20b. Therefore, this location adjustment of the stopper 3 enables the adjustment of the advancing amount of the lancet holder 1, whereby the lancet L can attain a desired lancing depth in the skin 99. The sleeve 20c, easy to rotate, provides good operationality. Further, the sleeve 20c, a part of the housing 2, is utilized for operation. This simplifies the structure of the lancing device A.

Figure 4A:
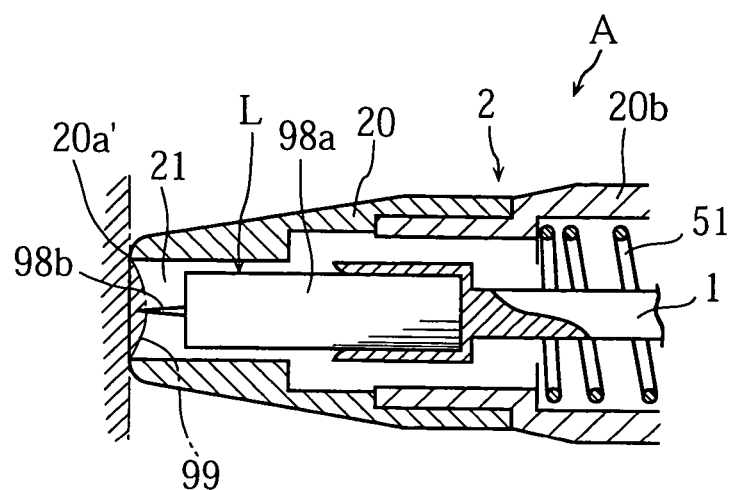
FIGS. 4A and 4B are explanatory views illustrating the operation of the lancing device shown in FIG. 1.
Figure 4B:
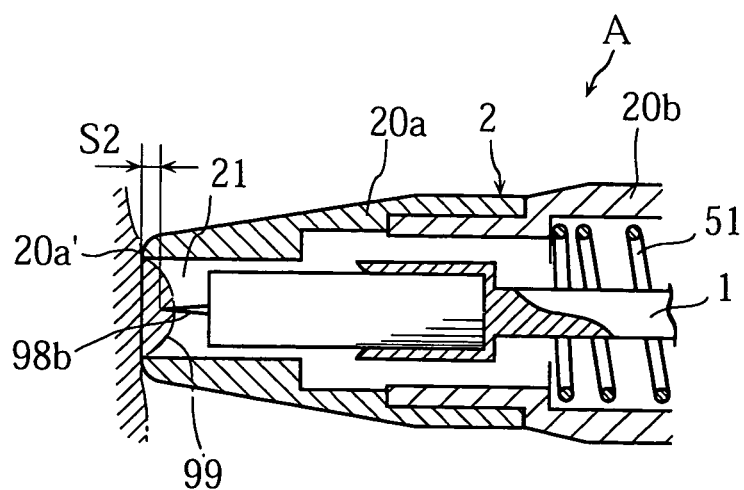

As shown in FIG. 3B, with the lancet L advanced, the needle 98b projects forward from the tip end portion 20a' by an appropriate dimension S1. In the lancing device A1, the location adjustment of the stopper 3 can vary the degree of the advancement. For example, the adjustment may be made so that the point of the needle 98b, as shown in FIG. 4A, may be located at the tip end portion 20a' of the housing 2, or that the point of the needle 98b, as shown in FIG. 4B, may be located inward from the tip end portion 20a' of the housing 2 by an appropriate dimension S2. Therefore, when only a small amount of blood sample is required, the lancet L may be caused to stick into the skin 99 with the advancing degree of the lancet holder 1 rendered small, as shown in FIG. 4A or 4B. In this case, the skin 99 needs to bulge into the opening 21 of the housing 2. This bulge of the skin 99 can occur merely by pressing the tip end of the housing 2 against the skin. 99, if the skin is soft. Though not shown in the figure, use may be made of a suction device (a negative pressure generator) for producing negative pressure in the opening 21, so that the skin 99 bulges to a greater degree. The lancing device of the present invention may incorporate such a suction device.

When the tip end of the lancet L is not allowed to project outward from the housing 2, as shown in FIGS. 4A and 4B, the lancet L penetrates the skin 99 by only a small lancing depth. In this case, the projection 79 engages with a front portion of the cam groove 78. As described above, the inclination angle of the front portion of the cam groove 78 is small. Therefore, in a case where a small lancing depth is desired to be attained with the lancet L, the stopper 3 moves over a small distance even when the sleeve 20c is rotated through a relatively great rotation angle. This means that a fine adjustment is possible in varying the location of the stopper 3. Accordingly, when the lancing depth into the skin 99 by the lancet L is to be small, it is easy to perform precise adjustment to the forward movement of the lancet holder 1 for ensuring the desired lancing depth.

On the other hand, when the lancing depth into the skin 99 by the lancet L is made large, the projection 79 engages with a rear portion of the cam groove 78 having large inclination angle. Consequently, the location adjustment of the stopper 3 tends to be rough. However, this causes no inconvenience when the lancing depth is made large to obtain a large amount of blood, since there is no need to set the lancing depth of the lancet L to an exact value.

In the lancing device A1 of the present embodiment, as described above, the lancet L has a nonconstant adjustment rate in its lancing depth. When the lancing depth into the skin 99 by the lancet L is made small to obtain a small bleeding amount, the lancing depth of the lancet L can be adjusted more finely than is possible when the lancing depth of the lancet L is large. Consequently, the lancing device A is user-friendly and satisfies user needs. Further, when the lancet L sticks into the bulging skin 99, the bleeding after lancing is facilitated. Thus, the lancing depth of the lancet L can be made small. The small lancing depth is preferable since the skin 99 does not suffer great damage.

Figure 5:
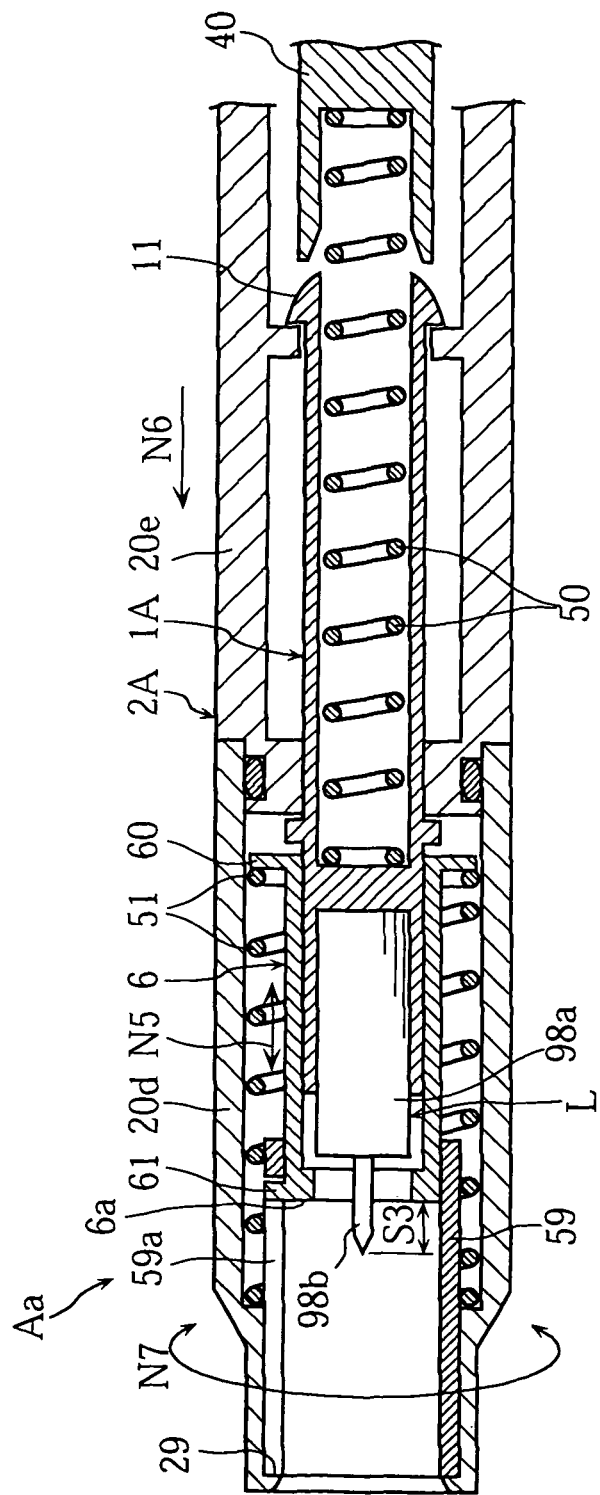
FIG. 5 is a sectional view showing a second embodiment of the lancing device according to the present invention.
Figure 6:
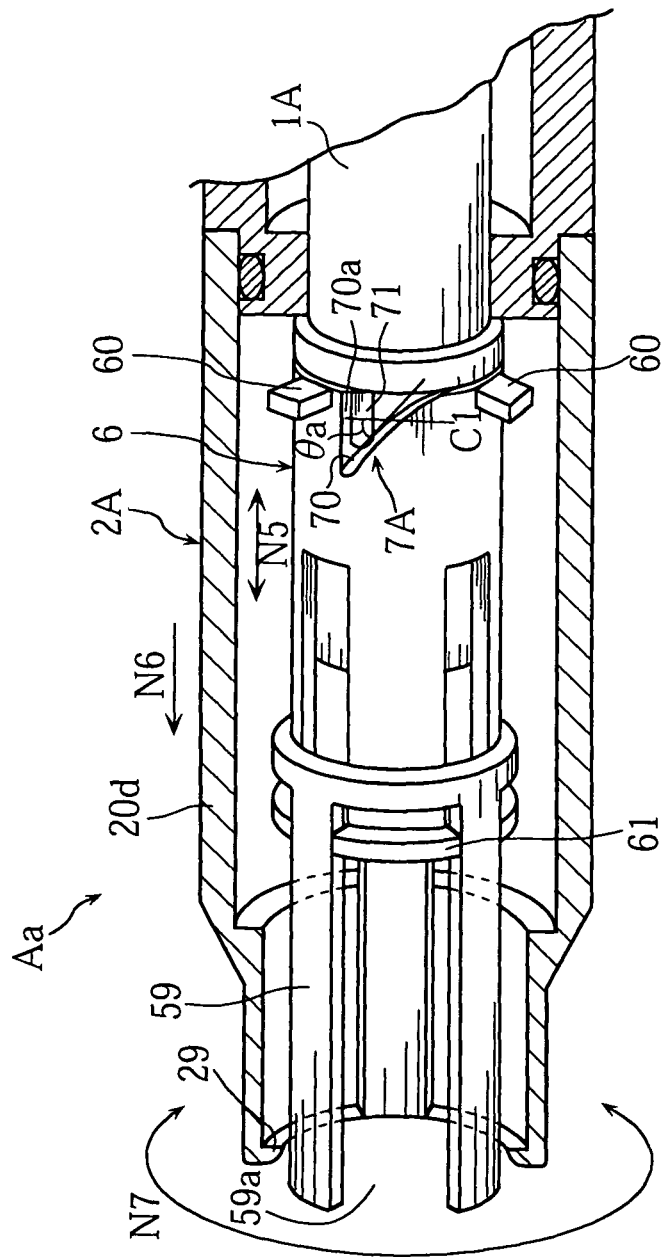
FIG. 6 is a perspective sectional view illustrating a principal portion of the lancing device shown in FIG. 5.
Figure 7:
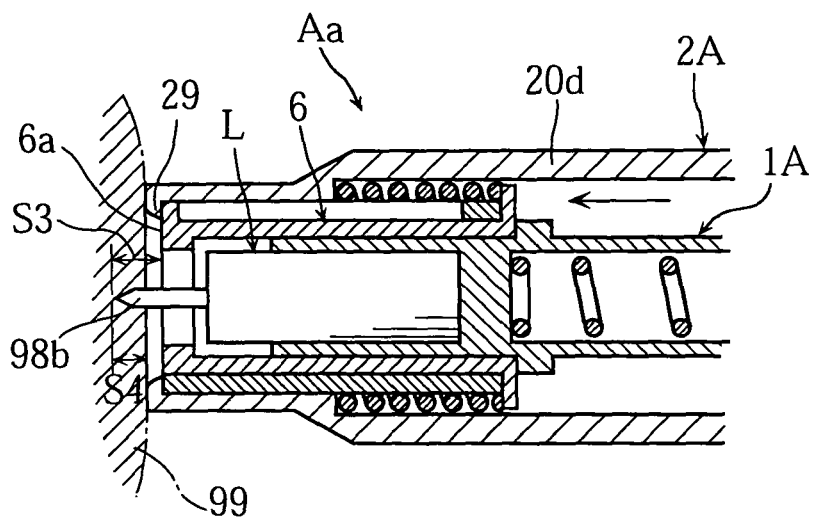
FIG. 7 is an explanatory view illustrating an operation of the lancing device shown in FIGS. 5 and 6.

FIGS. 5 through 7 illustrate a second embodiment of the present invention. In FIG. 5 and the succeeding figures, elements which are identical or similar to those of the first embodiment are designated by the same reference signs as those used in the first embodiment.

As clearly shown in FIGS. 5 and 6, a lancing device Aa of the present embodiment includes an auxiliary member 6 fitted around a tip end portion of a lancet holder 1A and a cam mechanism 7 for moving the auxiliary member 6 in the axial direction of the lancet holder shown by an arrow N5. The auxiliary member 6 has a rear end portion formed with a cam surface 70 contacting a projection 71 of the lancet holder 1A as described later. Consequently, when the lancet holder 1A moves forward in the direction designated by an arrow N6, the auxiliary member 6 moves together with it in the same direction. As in the first embodiment described above, the lancet holder 1A is caused to move forward after a latch pawl 11 is pressed by a pressing member 40.

A housing 2A includes a sleeve 20d having a tip end portion formed with an inward projection 29 for preventing the auxiliary member 6 from moving forward beyond a predetermined distance. The rear end portion of the auxiliary member 6 is formed with projections 60 to contact a return spring 51 (not shown in FIG. 6). After moving forward together with the lancet holder 1A, the auxiliary member 6 is retracted together with the lancet holder 1A by an appropriate amount by the resilient force of the spring 51. The sleeve 20d of the housing 2A is inwardly provided with a guiding member 59 for guiding the auxiliary member 6 in its reciprocal movement.

When the sleeve 20d is rotated relative to a sleeve 20e in the direction of an arrow N7, the auxiliary member 6 is also rotated in the same direction. Specifically, the auxiliary member 6 has a tip end circumference formed with projections 61 engaging into slits 59a of the guiding member 59, so that the auxiliary member 6 rotates together with the guiding member 59. The guiding member 59 rotates together with the sleeve 20d. As a result, the auxiliary member 6 is rotatable together with the sleeve 20d.

A cam mechanism 7A includes a cam surface 70 formed by providing a recess 70a on the outer circumferential surface of the auxiliary member 6 and includes a projection 71 formed on the lancet holder 1A for contact with the cam surface 70. The cam surface 70 inclines relative to a line C perpendicular to the axial direction of the lancet holder 1A. Consequently, when the auxiliary member 6 is rotated around its axis to shift the contact portion of the projection 71 with the cam surface 70, the auxiliary member 6 can move relative to the lancet holder 1A in the direction of the arrow N5. The cam surface 70 has position-dependent varying inclination angles, as does the cam groove 78 of the first embodiment. The inclination angle θa of the cam surface 70 gradually decreases toward the rear end portion of the auxiliary member 6. The tip end portion of the auxiliary member 6 surrounds a needle 98b of the lancet holder 1A. The needle 98b can project beyond a tip end surface 6a of the lancet L. It is desirable that the tip end portion of the auxiliary member 6 is cylindrical and completely surrounds the needle 98b. However, differing from such a structure, the tip end portion of the auxiliary member 6 may exist on only one side of the needle 98b.

In the lancing device Aa, as shown in FIG. 7, when the lancet holder 1A moves forward to cause the needle 98b of the lancet L to stick into the skin 99, the lancet holder 1A advances until the tip end surface 6a of the auxiliary member 6 contacts the inner projection 29 of the sleeve 2d for example, thereafter makes no further advancing movement. Further, though not illustrated in the figure, when the skin 99 bulges to enter an opening 21 of the housing 2A beyond the inner projection 29, differing from the above, the lancet holder 1A advances until the tip end surface 6a of the auxiliary member 6 contacts the skin 99, thereafter makes no further advancing movement. Therefore, in both cases, the lancet L has a lancing depth S4 into the skin 99 corresponding to a lancing depth S3 of the needle 98b of the lancet L from the tip end surface 6a of the auxiliary member 6.

In the lancing device Aa, rotating the sleeve 20d causes the auxiliary member 6 to move in the direction of the arrow N5, thereby varying the lancing depth S3 of the needle 98b of the lancet L from the tip end surface 6a of the auxiliary member 6. Therefore, the lancing depth into the skin by the lancet L can be appropriately adjusted by varying the amount S3.

When the lancing depth into the skin by the lancet L is made small, the projection 71 contacts a back portion of the cam surface 70. The back portion of the cam surface 70 slants gently. Thus, in adjusting the lancing depth of the lancet L in the area where the lancing depth is made small, the amount of forward and backward movement of the auxiliary member 6 is small relative to the amount of rotating the sleeve 20d, which enables fine adjustment.

Figure 8A:
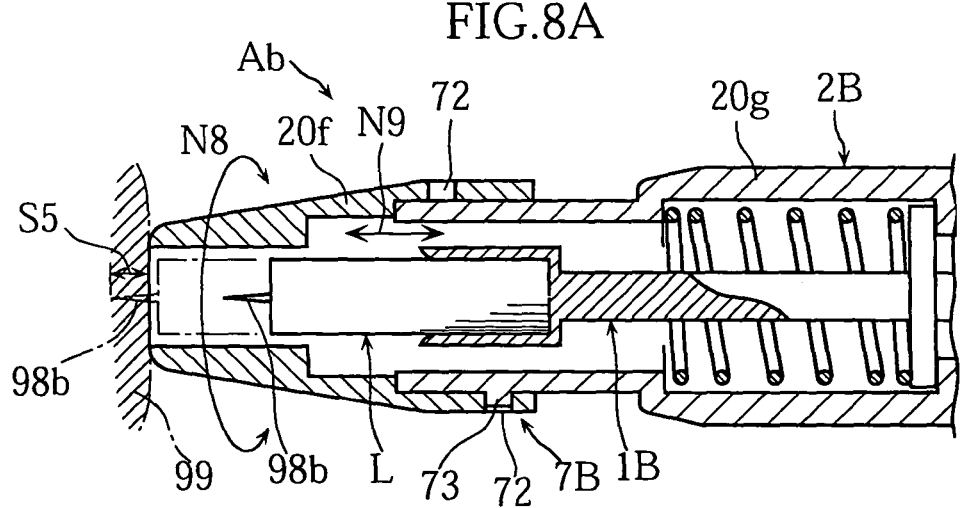
FIG. 8A is a sectional view illustrating a principal portion of a third embodiment of the lancing device according to the present invention.
Figure 8B:
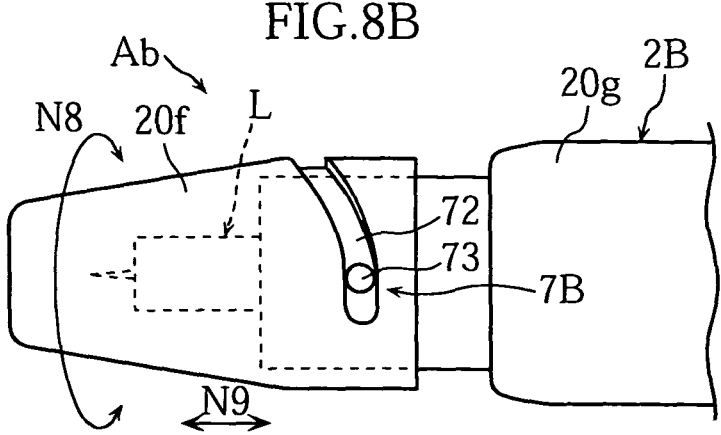
FIG. 8B is a lateral view illustrating the principal portion.

FIGS. 8A and 8B illustrate a third embodiment of the present invention. In a lancing device Ab of the present embodiment, a housing 2B includes a first sleeve 20f rotatable relative to a second sleeve 20g in the direction designated by an arrow N8. This rotation causes the first sleeve 20f to move reciprocally relative to the second sleeve 20g in the axis direction of the housing 2B and a lancet holder 1B designated by an arrow N9. More specifically, the lancing device Ab has a cam mechanism 7B including a cam groove 72 formed in the first sleeve 20f and a projection 73 formed on the second sleeve 20g for engaging in the cam groove 72. The cam groove 72 has inclination angle (angle relative to a line perpendicular to the axial direction of the housing 2B and the lancet holder 1B) that decreases toward the back portion of the first sleeve 20f (toward the right side of the figure).

In the lancing device Ab, the lancing depth into the skin 99 by the lancet L can be adjusted by rotating the first sleeve 20f so that the sleeve 20f shifts forward or backward in the direction of the arrow N9. In the lancing device Ab, changing the position of the tip end of the first sleeve 20f varies the sticking amount S5 of the needle 98b of the lancet L from the tip end of the first sleeve 20f. As a result, the lancing depth into the skin 99 by the lancet L changes. The further the first sleeve 20f moves forward, the smaller the lancing depth into the skin 99 by the lancet L becomes. When the lancing depth of the lancet L is made small, the projection 73 of the cam mechanism 7B engages with the back portion of the cam groove 72 slanting gently. Therefore, as in the first and second embodiments described above, when the lancing depth of the lancet L is made small, the fine adjustment of the lancing depth can be performed, whereby the adjustment of the lancing depth is performed easily and properly.

The present invention is not limited to those embodiments described above. Specifics of the members and components can be varied in many ways.

In the above-described embodiments, the fine adjustment of the lancing depth of the lancet L is performed when the lancing depth of the lancet L is made small rather than when the lancing depth of the lancet L is made large. However, the present invention is not limited to this. In accordance with the present invention, differing from the above, the fine adjustment of the lancing depth may be made possible when the lancing depth of the lancet is large rather than when the lancing depth of the lancet is small. Or the fine adjustment may be made possible when the lancing depth is intermediate rather than when the lancing depth is small or large. A user can choose one among these structures according to their needs. Any structure is within the scope of the present invention as long as the lancing depth into the lancing target by the lancet L is in a non-linear relationship with the operation amount of the operation member. The meaning of "non-linear" in the present invention has already been described above.

Figure 9:
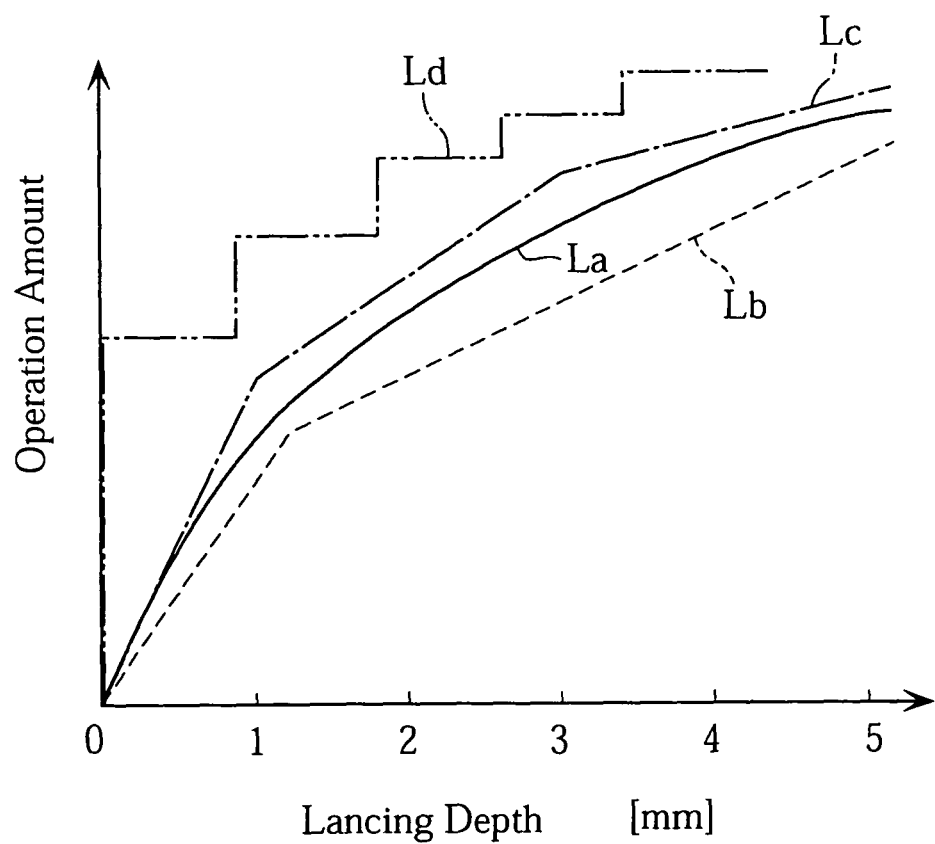
FIG. 9 is a graph showing a relationship between a lancing depth and an operation amount.

In the present invention, the lancing depth of the lancet and the operation amount of the operation member may have a relationship shown by a curve La in FIG. 9 in which the adjustment rate of the lancing depth varies gradually. Further, the lancing depth and the operation amount may have a relationship shown by a polygonal line Lb, Lc in FIG. 9 in which the adjustment rate of the lancing depth varies with a multi phase, for example two or three phases. Further, the lancing depth and the operation amount may have a relationship shown by a stepped line Ld in FIG. 9 in which the lancing depth varies by an appropriate amount at each step.

In the present invention, various operation mechanisms can be used for advancing the lancet from the inside toward the tip end portion of the housing. For example, the lancet may be arranged in the housing without using the lancet holder and may be moved forward by the resilient force of a spring or the like. Further, the lancet may be moved forward by being hit with an appropriate member. The lancet may vary in size and shape depending on its structure.

The lancing adjustment mechanism may utilize a different cam mechanism from the cam mechanism described above or may utilize a mechanism other than the cam mechanism.

The invention claimed is:

1. A lancing device for sampling blood or other body fluid comprising:
   a housing having an open tip end;
   an operation mechanism for advancing a lancet from inside the housing toward the tip end of the housing; and
   a lancing adjustment mechanism including an operation member which is operated for adjusting a lancing depth of the lancet into a target portion upon a maximum forward movement of the lancet by the operation mechanism;
   wherein the lancing adjustment mechanism provides a nonlinear relationship between the lancing depth of the lancet and an operation amount of the operation member; and
   wherein the lancing depth adjustable mechanism selectively provides a first lancing state in which a tip end of the lancet projects out beyond the tip end of the housing upon the maximum forward movement of the lancet and a second lancing state in which the lancet does not project out upon the maximum forward movement of the lancet, the lancet in the second lancing state sticking into the target portion bulging into the open tip end of the housing, the lancing depth varying at a lower rate for a given operation amount of the operation member in the second lancing state than in the first lancing state;
   wherein the operation mechanism advances the lancet to the lancing depth adjusted by the operation member of the lancing adjustment mechanism.

2. The lancing device according to claim 1, wherein the lancing adjustment mechanism includes a stopper for stopping the forward movement of the lancet by contacting the lancet or a member forwardly movable with the lancet, and wherein the stopper is reciprocally movable axially of the housing by operating the operation member.

3. The lancing device according to claim 2, wherein the operation member is a rotatable sleeve, the stopper being arranged in the housing to rotate together with the sleeve when the sleeve is rotated, the housing and the stopper being formed with a cam groove and a projection for moving the stopper axially of the housing, the projection engaging in the cam groove.

4. The lancing device according to claim 3, wherein the cam groove has different inclination angles toward a forward and a rear ends, respectively, of the housing.

5. The lancing device according to claim 3, wherein the sleeve forms a part of the housing.

6. The lancing device according to claim 1, wherein the lancing adjustment mechanism includes an auxiliary member fowardly movable together with the lancet within the housing toward the tip end of the housing, the auxiliary member having a tip end flanking a tip end of the lancet, the lancet projecting beyond the tip end of the auxiliary member by an amount which is variable by operating the operation member.

7. The lancing device according to claim 6, wherein the tip end of the auxiliary member is cylindrical to surround the tip end of the lancet.

8. The lancing device according to claim 6, wherein the operation mechanism comprises a lancet holder arranged in the housing for holding and advancing the lancet, the operation member being a rotatable sleeve, the auxiliary member being fitted into the lancet holder to rotate together with the sleeve when the sleeve is rotated, the auxiliary member and the lancet holder being formed with a cam surface and a projection contacting each other for moving the auxiliary member axially of the housing by rotating the auxiliary member.

9. The lancing device according to claim 8, wherein the cam surface has different angles toward a forward and a rear ends, respectively, of the housing.

10. The lancing device according to claim 1, wherein the housing includes a first sleeve forming the tip end of the housing and a second sleeve connected to a rear end of the first sleeve, the lancing adjustment mechanism enabling the first sleeve to move reciprocally relative to the second sleeve axially of the housing by rotating the first sleeve relative to the second sleeve.

11. The lancing device according to claim 10, the lancing adjustment mechanism comprises a cam mechanism including a cam groove and a projection formed on the first sleeve and the second sleeve, the projection engaging in the cam groove, the cam groove having different angles toward a forward and a rear ends, respectively, of the housing.

12. A lancing device for sampling blood or other body fluid comprising:
   a housing having an open tip end;
   an operation mechanism for advancing a lancet from inside the housing toward the tip end of the housing; and
   a lancing adjustment mechanism including an operation member which is operated for adjusting a lancing depth of the lancet into a target portion upon maximum possible forward movement of the lancet by the operation mechanism;
   wherein the lancing adjustment mechanism provides a nonlinear relationship between the lancing depth of the lancet and an operation amount of the operation member;
   wherein the lancing depth adjustable mechanism selectively provides a first lancing state in which a tip end of the lancet projects out beyond the tip end of the housing upon maximum possible forward movement of the lancet and a second lancing state in which the lancet does not project out upon maximum possible forward movement of the lancet, the lancing depth varying at a lower rate for a given operation amount of the operation member in the second lancing state than in the first lancing state; and
   wherein the operation mechanism advances the lancet to the lancing depth adjusted by the operation member of the lancing adjustment mechanism.

\* \* \* \* \*